United States Patent [19]
Asaeda et al.

[11] Patent Number: 5,734,742
[45] Date of Patent: Mar. 31, 1998

[54] INSPECTION SYSTEM AND PROCESS

[75] Inventors: Teruo Asaeda, Tokyo; Kazunori Nousou, Yokohama; Masanori Imanisi, Tokyo; Yutaka Suzuki, Zama; Sachiyo Katabami, Yokosuka, all of Japan

[73] Assignee: Nissan Motor Co., Ltd., Kanagawa, Japan

[21] Appl. No.: 528,868

[22] Filed: Sep. 15, 1995

[30] Foreign Application Priority Data

Sep. 19, 1994 [JP] Japan .................................. 6-223471

[51] Int. Cl.⁶ ............................................ G06K 9/00
[52] U.S. Cl. ............................................ 382/141; 382/107
[58] Field of Search ................................ 382/103, 104, 382/107, 141, 149; 248/92, 94, 125, 126

[56] References Cited

U.S. PATENT DOCUMENTS

| 4,396,903 | 8/1983 | Habicht et al. | 382/103 |
| 5,027,413 | 6/1991 | Barwood | 382/103 |
| 5,243,418 | 9/1993 | Kuno et al. | 382/103 |
| 5,247,584 | 9/1993 | Krogmann | 382/107 |
| 5,249,238 | 9/1993 | Komerath et al. | 382/107 |
| 5,260,557 | 11/1993 | Kissh et al. | 382/103 |
| 5,600,731 | 2/1997 | Sezan et al. | 382/107 |

FOREIGN PATENT DOCUMENTS

| 2-73139 | 3/1990 | Japan . |
| 5-45142 | 2/1993 | Japan . |
| 5-45143 | 2/1993 | Japan . |
| 5-45144 | 2/1993 | Japan . |

Primary Examiner—Joseph Mancuso
Attorney, Agent, or Firm—Lowe, Price, LeBlanc & Becker

[57] ABSTRACT

In order to reliably detect a defect on an inspected surface, electronic pictures of the inspected surface are formed at different positions by moving an imaging area relative to the inspected surface. Defect candidate regions are extracted from a series of the pictures. The system examines whether a movement from one candidate region to another candidate region is proportional to the movement of the imaging area. If the movement between the candidate regions is in proportion to the movement of the imaging area, the system judges that the candidate regions are imagery of a defect on the inspected surface.

21 Claims, 7 Drawing Sheets

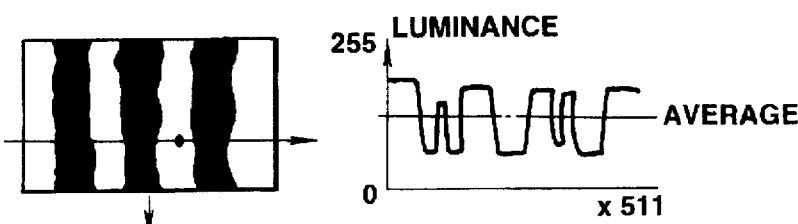
FIG.6A(1)
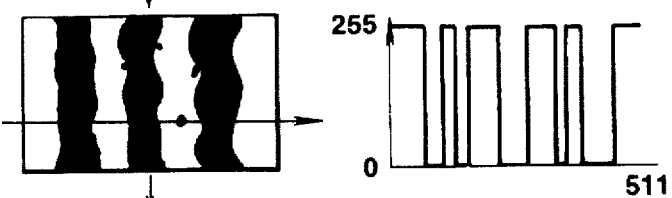
FIG.6A(2)
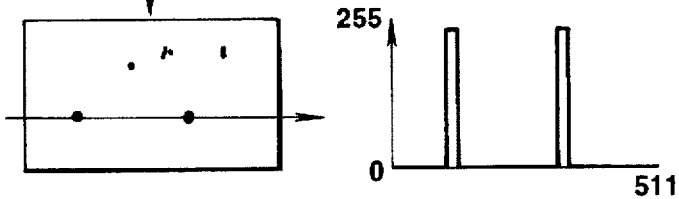
FIG.6A(3)
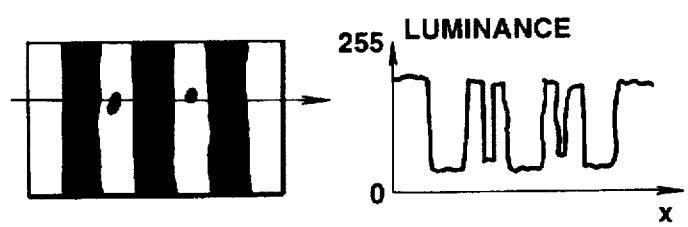
FIG.6B(1)
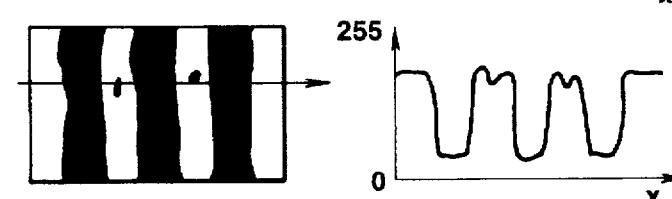
FIG.6B(2)
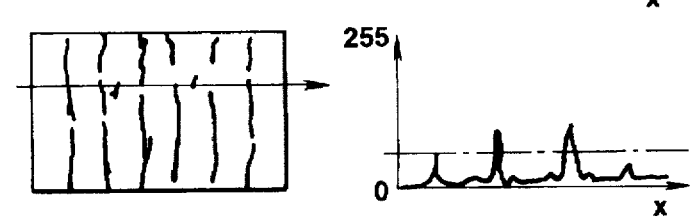
FIG.6B(3)
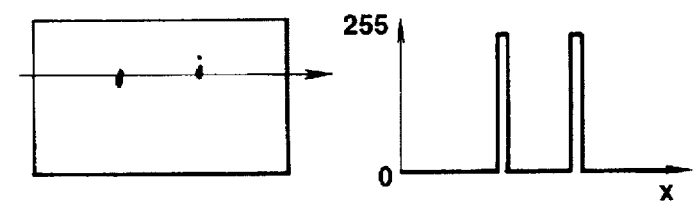
FIG.6B(4)

INSPECTION SYSTEM AND PROCESS

BACKGROUND OF THE INVENTION

The present invention relates to inspection system and process for optical inspection of products or other objects, and more specifically to inspection system and process for detecting flaws on a surface of a product such as a coated surface of a panel for motor vehicles in automotive production process.

Japanese Patent Provisional (unexamined) Publications Nos. 2(1990)-73139, 5(1993)-45142, 5(1993)-45143, 5(1993)-45144 disclose conventional examples of the optical inspection system. These conventional examples are arranged to radiate a striped pattern having an alternate arrangement of bright and dark stripes on a painted surface to be inspected, and to detect flaws or defects on the painted surface by differentiating an image to find changes in luminance (brightness) due to flaws on the painted surface.

These conventional inspection systems are designed to process each of image pictures as a still picture, however, so that a noise may be misjudged as a flaw or defect.

When an object to be inspected is moved, an image sensor camera may fail to catch a defect on the object because of an influence of timing of image formation, for example. In such a case, the nonexistence of a defect in an electronic picture taken by the camera readily leads to a failure in detecting the defect.

At or near a boundary between stripes (that is, a boundary between a bright zone and a dark zone), these systems have difficulty in detecting a defect which is too shallow in angle for image formation.

SUMMARY OF THE INVENTION

It is therefore an object of the present invention to provide inspection system and/or process which can improve the accuracy in flaw detection.

According to the present invention, each of inspection process and system for detecting a defect on an inspected surface, such as a painted surface, of an object to be inspected comprises an image producing step or means and an image processing step or means.

The image producing step or means is for moving the inspected surface relative to an imaging area, or a field of view of an imaging means such as a CCD camera, and forming a sequence of electronic pictures of the inspected surface within the imaging area with the imaging means. This movement is implemented by moving either or both of the inspected surface and the imaging area.

The image processing step or means is for extracting a set of defect candidate regions from the pictures, for determining a spatial separation from a position of one candidate region, extracted from a previous picture which is one of the pictures, to a position of another candidate region extracted from a subsequent picture, which is one of the pictures formed after the previous picture by the image producing means. This step or means determines whether the spatial separation is in agreement with a movement of said inspected surface relative to said imaging area, and judges that there exists a defect in the inspected surface when the spatial separation is in agreement with the movement.

In one example of the present invention, the image producing step or means comprises an imaging step or means for forming the electronic pictures and a moving step or means for moving at least one of the object to be inspected, and the imaging means which determines said imaging area. The image processing step or means comprises an extracting step or means for extracting the set of the candidate regions, as well as an examining step or means for examining positions of the candidate regions extracted from at least two of the pictures. The examining step or means also determines a quantity of a positional change from the position of one candidate region, extracted from the previous picture, to the position of another candidate region, extracted from the subsequent picture. The examining step or means also examines whether the quantity of the positional change is substantially proportional to a quantity of movement of the inspected surface relative to the imaging area. In this example of the present invention, the image producing step or means also includes a deciding step or means for deciding that there exists a defect on the inspected surface when the quantity of the positional change is substantially proportional to the quantity of movement of the inspected surface.

The inspected system and process according to the present invention are thus arranged to select a series of two or more defect-like object regions extracted from two or more of the sequence of the pictures, and examine whether the series of the defect-like object regions is a spatiotemporal series of images of a defect on the moving object or not, by comparing the spatial intervals among the defect-like object regions in the series with the distances of movement of the inspected surface within the imaging area during time intervals of image formation. Therefore, the inspection system and process according to the present invention can distinguish more exactly between defects and noises, and improve the accuracy of detection.

The image producing means according to the present invention may further comprises an illuminating means for projecting a bright and dark pattern on the inspected surface in the imaging area, so that each picture taken by the imaging means is an image of the bright and dark pattern shed on the inspected surface. The use of the bright and dark pattern facilitates the detection of a defect such as a depressed or raised portion in a painted surface. The system and process of the present invention can make a clearer discrimination between defects and noises in the imagery of the bright and dark pattern.

The inspection system and process according to the present invention may be arranged to affirm the existence of a defect only when a plurality of defect-like object regions equal to or greater in number than a predetermined integer M (M=3, for example) are arranged in a manner of a time series of images of an object moving with the inspected surface. By thus examining three or more pictures to find a track of a moving object, the inspection system and process can discriminate between noise and defect more reliably.

The inspection system and process may be arranged to extract defect-like object regions located in the bright zones of the imagery of the bright and dark pattern and to examine only the positions of the defect-like object regions extracted from the bright zones. In this case, the number of the defect-like object regions which must be examined is reduced, and the inspection system and process can detect a defect accurately and speedily.

BRIEF DESCRIPTION OF THE DRAWINGS

FIGS. 6A(1), 6A(2) and 6A(3) are views for illustrating one extracting method which can be employed in the inspection system and process according to the present invention.

FIGS. 6B(1), 6B(2), 6B(3) and 6B(4) are views for illustrating another extracting method which can be employed in the inspection system and process according to the present invention.

DETAILED DESCRIPTION OF THE INVENTION

Figure 1:
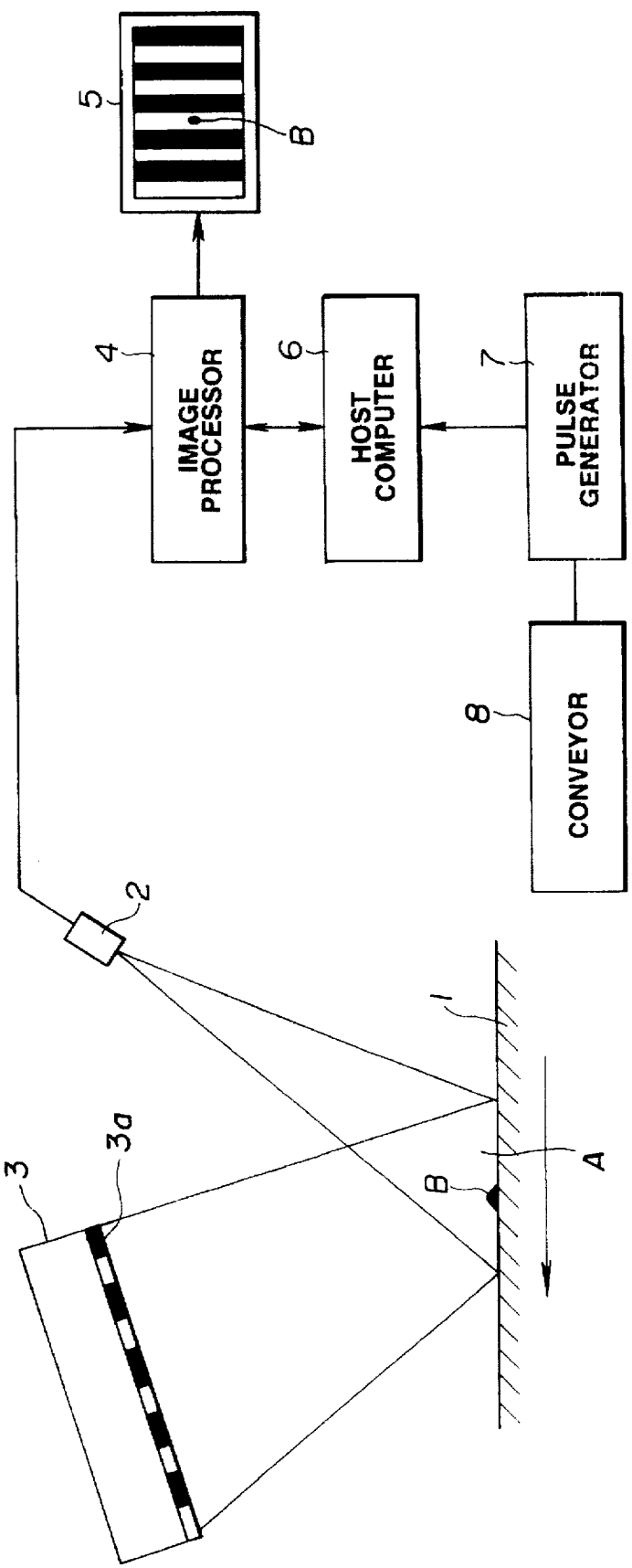
FIG. 1 is a block diagram schematically showing an arrangement of an inspection system for defect detection according to one embodiment of the present invention.

FIG. 1 schematically shows an inspection system for performing an inspection process according to one embodiment of the present invention.

An inspected surface 1 is a surface of an object to be inspected. For example, the inspected surface 1 is a painted or coated surface of a vehicle body carried into an inspection site from a painting booth (or spray booth) by a conveyor 8. Since the quality of the painted surface is subtlely influenced by factors such as the concentration of the paint and the coated paint weight (or coverage), this inspection system is designed to measure the property of the painted surface quantitatively.

A camera 2 having a CCD imager is aimed at the inspected surface. The CCD camera 2 can serve as an imaging means. The CCD camera 2 can form an electronic image of the inspected surface within an imaging area A in a field of view of the camera 2.

An illuminating device 3 of this example has a stripe grid 3a for radiating a bright and dark striped pattern in the imaging area A on the inspected surface 1. The device 3 can serve as an illuminating means.

An image processor 4 receives pictures of the inspected surface 1 in the imaging area A from the camera 2. For example, the CCD camera 2 sends a sequence of pictures at regular intervals of a predetermine time, about 1/30 sec to the image processor 4. The image processor 4 has a storage device for storing the sequence of pictures produced at regular time intervals.

In this example, the inspected object surface 1 is moved along a direction shown by an arrow in FIG. 1, by the conveyor 8. In this example, the CCD camera 2 is provided on a path along which the vehicle body is carried by the conveyor 8. As the inspected surface 1 moves, the imaging area A sweeps over the inspected surface 1 along a predetermined straight line determined by the movement of the inspected surface. Therefore, pictures taken at regular time intervals are pictures of different areas of the inspected surface 1. The conveyor 8 can serve as a moving means for moving the inspected surface relative to the imaging area A.

A monitor 5 displays one still picture which is formed by the CCD camera 2 and processed by the image processor 4. An actual defect (or flaw) B (shown as a projection) on the painted surface 1 to be inspected is displayed as a defect B in the picture on the screen of the monitor 5.

In this example, the surface 1 to be inspected is moved whereas the camera 2 is stationary. It is however optional to arrange the image producing system so that the CCD camera 2 is moved to shift the imaging area A over the inspected surface 1.

A host computer 6 is connected with the image processor 4. The host computer 6 finally determines the existence or nonexistence of a defect or defects on the painted surface 1.

A pulse generator 7 generates a pulse signal representing a distance traveled by the inspected surface of the object carried by the conveyor 8. The amount of movement of the inspected surface 1 is represented by the number of pulses of the pulse signal. From the number of pulses (corresponding to the displacement of the object) from the pulse generator 7, and one or more candidate points for defects obtained from a plurality of the pictures taken successively at regular time intervals like a process of time series, the host computer 6 determines whether or not the amount of movement of each candidate point detected in the still pictures is proportional to the actual amount of movement of the object, that is, the amount of movement of the imaging area A relative to the inspected surface 1. If the amount of movement of any candidate point is proportional to the actual amount of movement of the imaging area A relative to the inspected surface 1, then the host computer 6 judges that this candidate point is really a defect on the painted surface.

The image processor 4 detects one or more defect candidate points in the following manner.

Figure 2A:
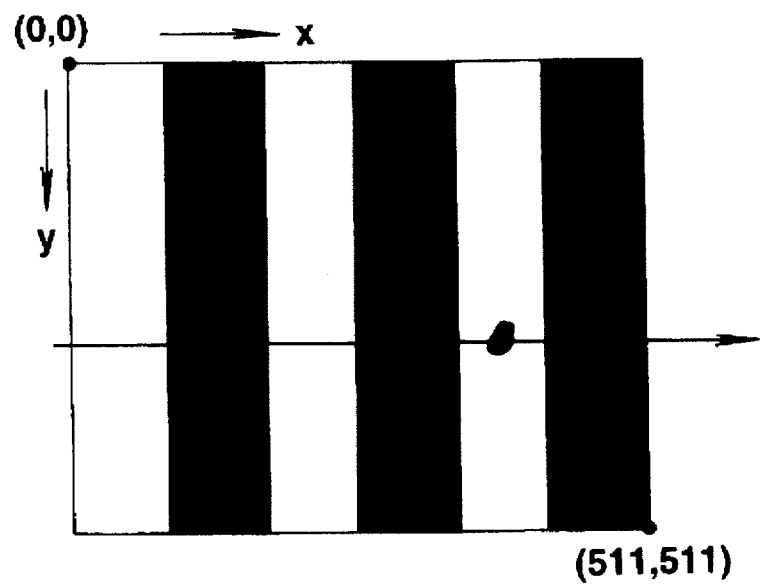
FIG. 2A is a schematic view showing, as an example, a picture taken by a CCD camera of the inspection system shown in FIG. 1.
Figure 2B:
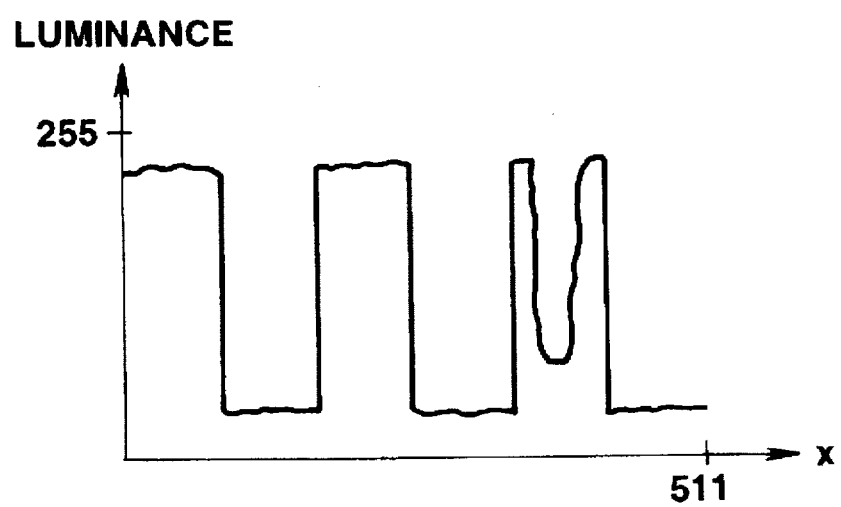
FIG. 2B is a graph showing a variation of a luminance along a predetermined line in the picture shown in FIG. 2A.

FIG. 2A schematically shows, as one example, a picture of the inspected surface 1 in the imaging area A taken by the CCD camera 2 at a certain instant. The picture displayed on the screen of the monitor 5 is an alternating pattern of bright and dark stripes because of the bright and dark pattern projected through the striped grid 3. The picture of FIG. 2A can be expressed in the form of a luminance signal waveform as shown in FIG. 2B. The luminance varies along a x direction as shown in FIG. 2B. The luminance (or brightness) is high in each of the bright stripes, and low in the dark stripes. In the example shown in FIGS. 2A and 2B, a defect candidate point exists in one of the bright zones, and appears as a low luminance isolated object region in a high luminance background. If this dark isolated region in the bright zone is equal to or greater than a predetermined size, then the image processor 4 regards this dark region as a defect candidate.

The inspection system according to this embodiment does not draw a conclusion merely from the detection of such a defect candidate, but further checks whether a defect candidate moves according as the imaging area A moves. A recognized defect candidate is judged to be a noise if the candidate does not move in pace with the movement of the imaging area A relative to the inspected surface 1. This inspection system is designed to discriminate a defect from a noise by examining the movement of a candidate.

Figure 3:
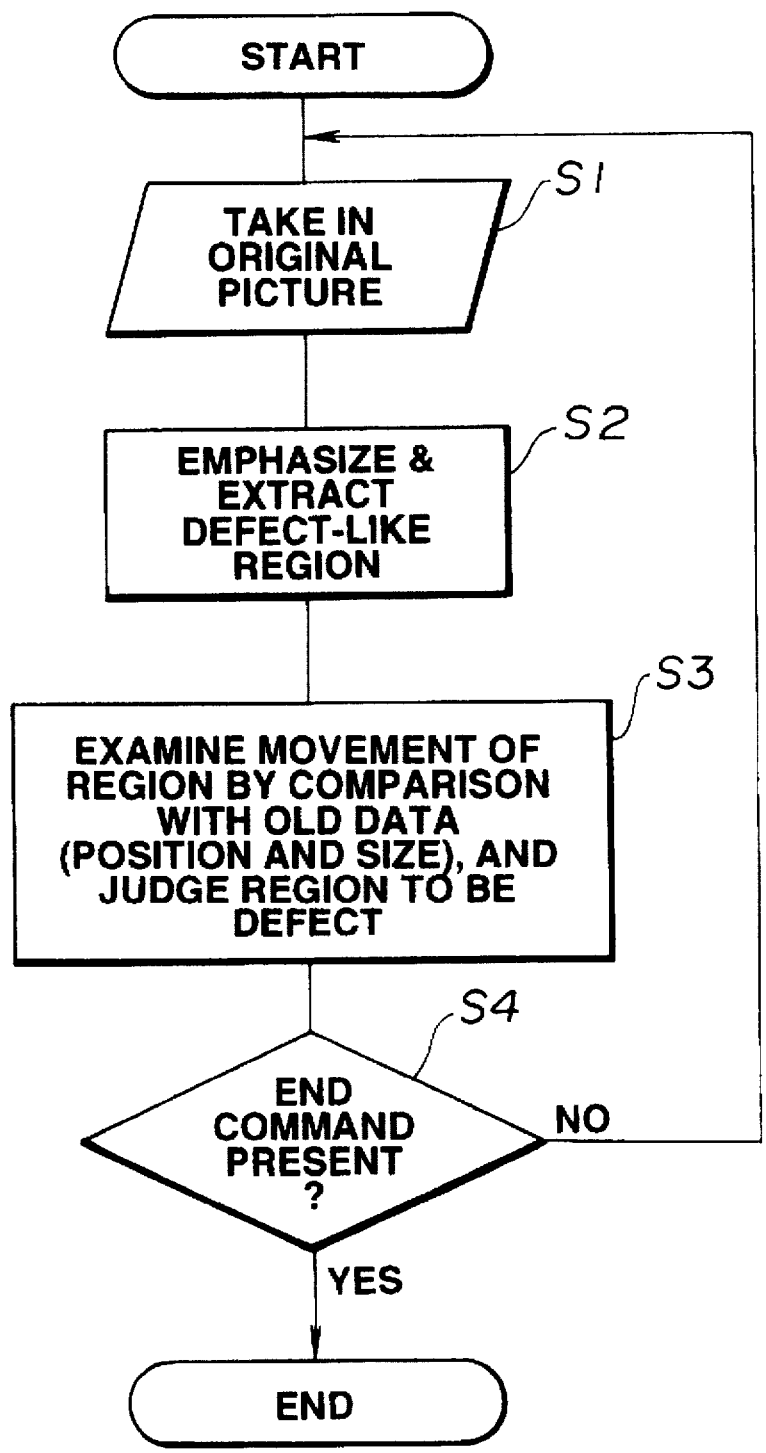
FIG. 3 is a flow chart showing an inspection process according to the present invention, performed by the inspection system of FIG. 1.

FIG. 3 shows an inspection process performed by the inspection system shown in FIG. 1.

At a step S1, the image processor 4 receives a picture of the inspected surface 1 in the imaging area A from the CCD camera 2, and stores the picture in the storage device.

At a step S2, the image processor 4 performs an emphasizing (or enhancement) operation on the stored picture to facilitate extraction of defects. As the emphasizing operation, it is possible to employ a known technique such as area or size discrimination. The processed picture is stored in another addressable memory section of the storage device.

At a step S3, the host computer 6 receives the processed picture obtained by the image processing, computes the amount of movement of each defect candidate extracted from the pictures by checking the position and size of the candidate, and judges any one or more of the candidates is a result of the existence of an actual defect on the painted surface if the movement of the defect candidate is in synchronism with the movement of the imaging area A that is measured from the pulse signal supplied from the pulse generator 7.

At a step S4, it is determined whether an end command signal is present or not, and the steps S1~S3 are repeated until the end command signal is issued from the outside.

By repeating the steps S1 and S2, a series of striped pictures are inputted and stored in the storage device, and processed by the image processor 4. The striped pictures are stored in the storage device in a manner of a time series, and the image processor 4 processes all the stored pictures by performing the emphasizing and defect extraction operation. The host computer 6 determines the amount of movement of each defect candidate by checking the positions and sizes of candidates extracted from the time series of the pictures.

Figure 4:
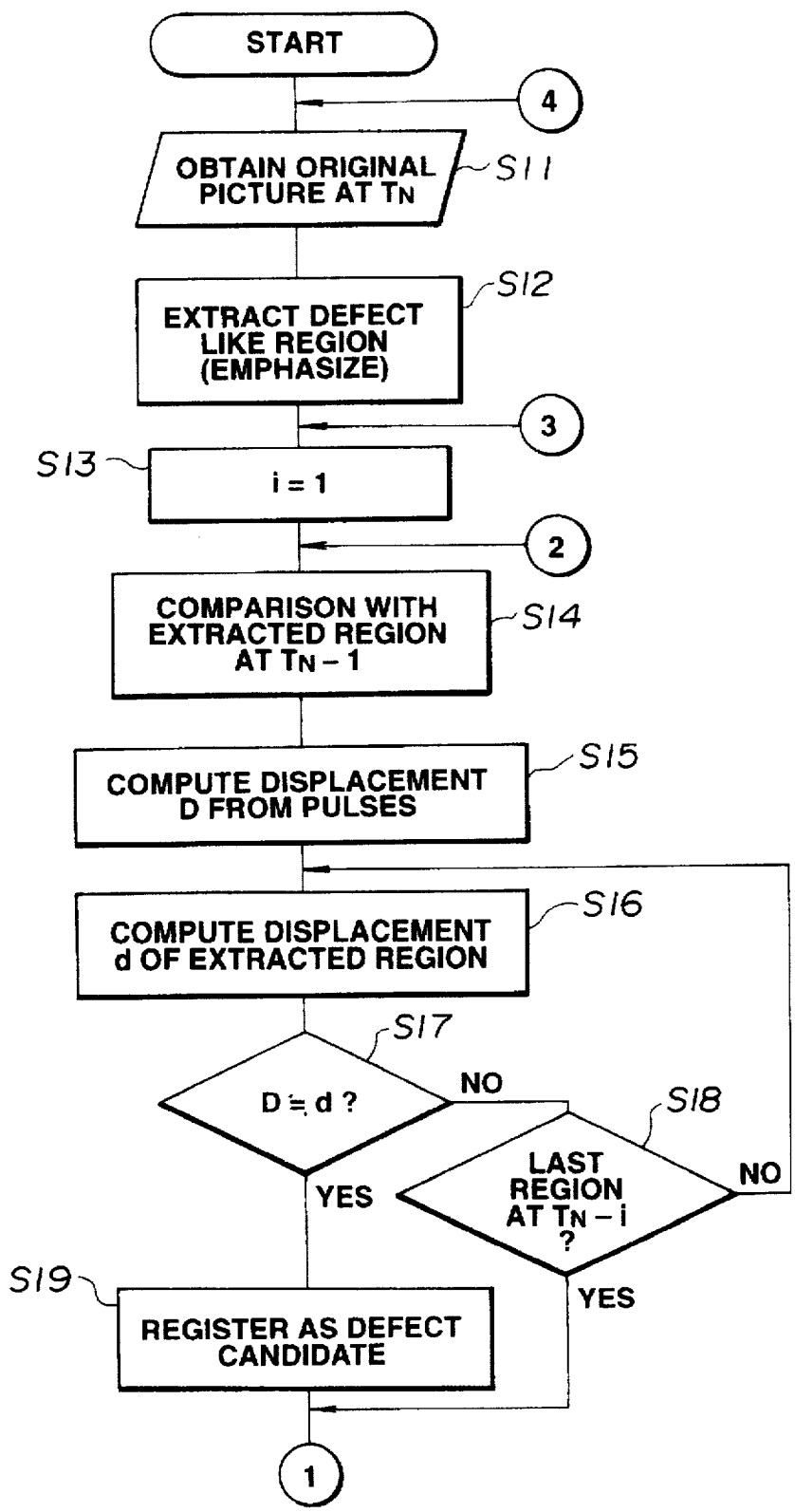
FIGS. 4 and 5 are flow charts showing the inspection process of FIG. 3 more in detail.
Figure 5:
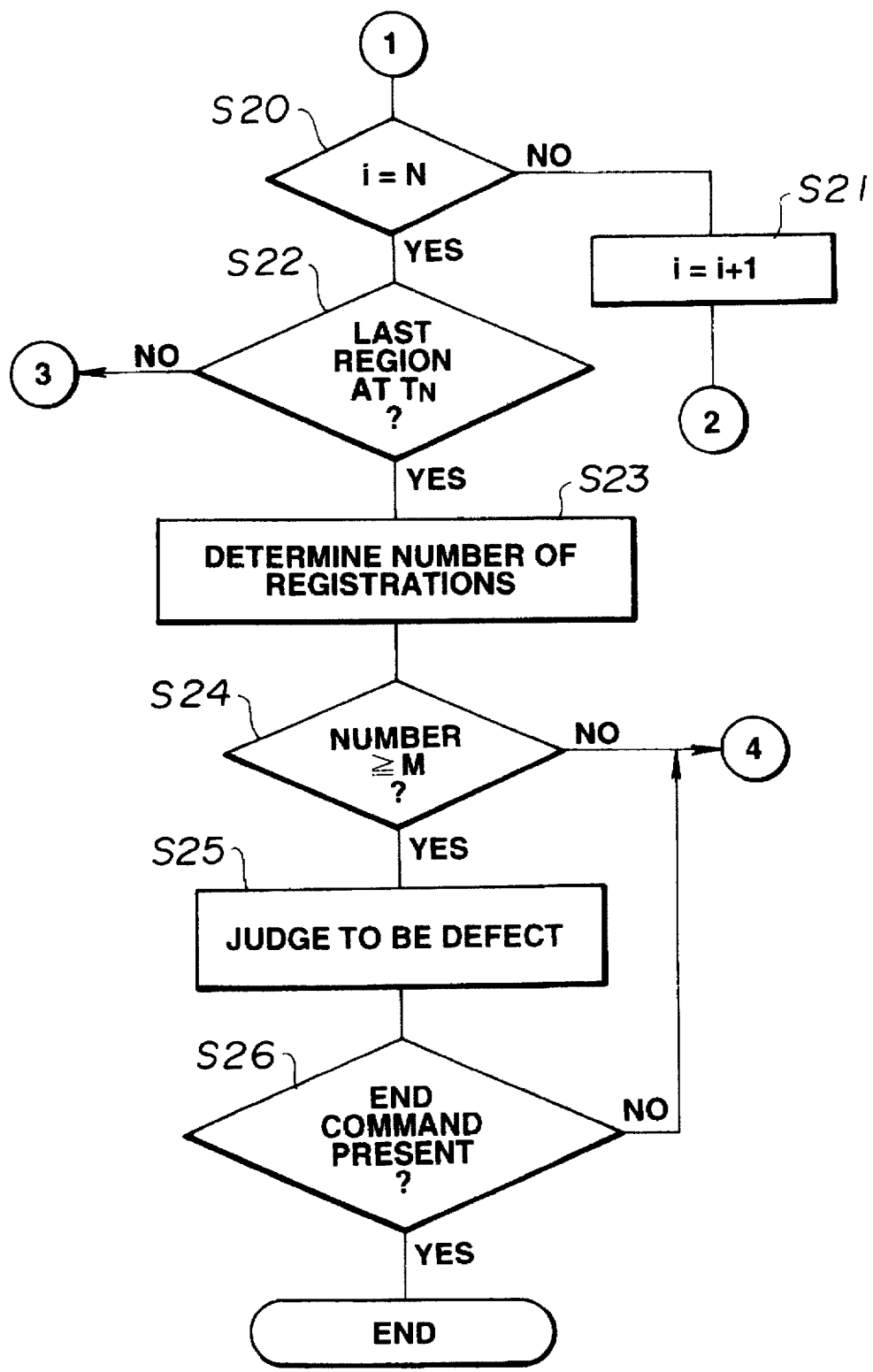

FIGS. 4 and 5 shows the inspection process according to the embodiment more in detail.

At a step S11, the CCD camera 2 forms an electronic picture of the striped pattern at a time instant TN, and the image processor 4 receives this original striped picture and stores the image date of the original striped picture in the storage section of the image processor 4. In this case, the inspection system resets, to zero, the count of pulses from the pulse generator 7 which is indicative of the position of the imaging area A of the CCD camera 2 relative to the inspected surface 1. This reset is done by the host computer 6 that operates in synchronism with the image processor 4.

At a step S12, the image processor 4 subjects the original striped picture stored in the storage section to the emphasizing operation to make it easy to extract a defect-like object region. In this emphasizing operation, the image processor 4 extracts one or more defect-like object regions, if any, from the original picture. The defect-like object region is an image region that is likely to be a defect.

FIGS. 6A(1), 6A(2) and 6A(3) show one example of the emphasizing and extracting operation. In this example, a defect-like object is extracted by area discrimination (or size discrimination). FIG. 6A(1) shows an original striped picture and a corresponding video wave form representing the luminance in the original striped picture. The image processor 4 converts this original picture to a binary image as shown in FIG. 6A(2) by a thresholding operation with a predetermined threshold level which, in this example, is an average of the luminance. Then, the image processor 4 extracts only regions having widths within a predetermined range. FIG. 6A(3) shows a picture and its luminance signal wave form obtained as the result of the extracting operation. The extracted region or each of the extracted regions is treated as a defect-like object region.

FIGS. 6B(1), 6B(2), 6B(3) and 6B(4) show another example employing a smoothing operation. FIG. 6B(1) shows an original striped picture and an original video wave form representing the luminance along the vertical axis of the rightside graph. The image processor 4 performs a smoothing operation on the original wave form, and by so doing, obtains a smoothed wave form as shown in FIG. 6B(2). FIG. 6B(2) shows a smoothed image picture and its luminance wave form obtained by the smoothing operation. Then, the image processor 4 performs a subtracting operation to determine the absolute value of a difference resulting from subtraction of the intensity of the smoothed wave form shown in FIG. 6B(2) from the intensity of the original wave form shown in FIG. 6B(1). FIG. 6B(3) shows a difference image picture and its wave form obtained by this subtracting operation. Then, the image processor 4 converts the difference image picture to a binary image by a thresholding operation with a predetermined threshold level. FIG. 6B(4) shows the resulting binary image picture and its wave form. In this example, two defect-like object regions are extracted.

Extraction of defect-like regions is possible by these methods and various other known methods.

At a step S13 in FIG. 4, the inspection system sets a picture counter for counting the number of pictures to a state indicating the count i is equal to one.

At a step S14, the inspection system compares the defect-like regions detected in the N−i numbered previous picture (i.e. the (N−i)th picture), and the N numbered current picture (i.e. the Nth picture). This comparison is not possible when there is only one picture. The comparison is performed after at least two of the pictures are obtained.

At a step S15, the host computer 6 counts the pulses outputted from the pulse generator 7, computes the position of the imaging area A in accordance with the pulse count reached by the pulse counting, and computes a displacement (or distance) D between the position of the imaging area A of the N−i numbered picture and the position of the imaging area A of the N numbered picture.

At a step S16, the host computer 6 computes a displacement (or distance) d between a first one of the defect-like regions extracted from the N numbered current picture and a first one of the defect-like regions extracted from the N−1 numbered previous picture.

At a step S17, the host computer 6 determines whether the displacement d is approximately equal to the displacement D.

A step S18 is reached if the answer of the step S17 is negative. At the step S18, the host computer 6 determines whether the last defect-like object region in the N−i previous picture taken at an instant TN−i has been examined. If not, the host computer returns to the step S16. Thus, if the displacement d between the first one of the defect-like objection regions in the N numbered picture and the first one of the defect-like object regions in the N−i picture is not in a range of D=d, then the host computer 6 examines the displacement d of the first defect-like region in the N numbered current picture, from a second one of the defect-like object region in the N−i numbered previous picture.

A step S19 is reached if the answer of the step S17 is affirmative. The currently examined defect-like region in the N numbered current picture is registered as defect candidate at the step S19 if the displacement d is approximately equal to D.

In the section of the steps S16~S19, the host computer 6 registers any defect-like object region extracted from the current picture as the defect candidate if the displacement d of that region from any one of the regions extracted from the previous picture matches the displacement D.

At a step S20 following the step S19, it is determined whether the count i is equal to N. If not, the count i is increased by one at a step S21, and the control is transferred to the step S14. If i=N, the host computer 6 determines whether the last defect like region in the N numbered current picture at the instant TN has been examined. The host computer 6 returns to the step S13 if the answer of the step S22 is negative, and proceeds to a step S23 if the answer of the step S22 is affirmative.

At the step S23, the host computer 6 determines the number of registrations of each defect-like object region in the N numbered current picture as the defect candidate.

At a step S24, the host computer 6 determines whether the number of registrations of each region is equal to or greater than a predetermined number M. If the number of registrations is equal to or greater than M, then the host computer 6 finally judges that the defect like object region is an image of an actual defect on the inspected surface 1. The host computer 6 determines, at a step S26, whether an end command signal is inputted, and repeats the operations of FIGS. 4 and 5 until the host computer 6 receives the end command signal.

In this way, the inspection system examines the defect-like object regions in all the previously acquired pictures to determine whether each of the defect like regions in the N numbered current picture is really a defect. When N=5, for example, the inspection system examines the previous four pictures obtained at the instants $T_{N-1}$, $T_{N-2}$, $T_{N-3}$ and $T_{N-4}$.

Even if one or more of the previous pictures lack an image of an actual defect for one reason or other, the inspection system of this example can detect the defect by examining all the previous pictures and the number of registrations as the defect candidate. It is, however, optional to examine only one or more of the previous pictures.

Figure 7:
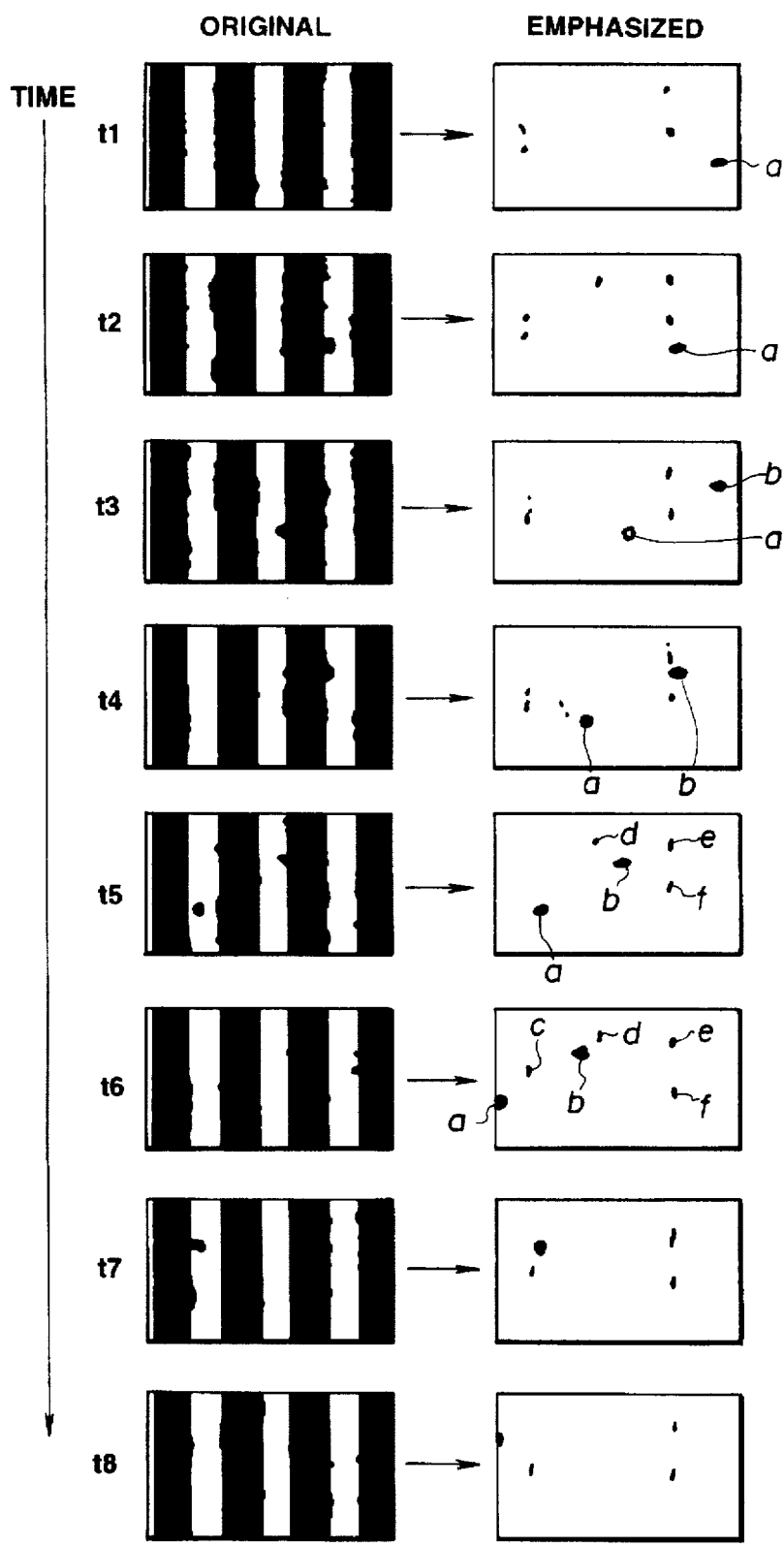
FIG. 7 is a view for illustrating a time series of original pictures and a time series of processed pictures processed by the inspection system according to the present invention.

FIG. 7 illustrates the process according to the embodiment of the present invention. The CCD camera 2 provides a time series of original striped pictures taken at instants t1–t8. From these original pictures, defect-like object regions are emphasized and extracted as shown on the right in FIG. 7.

The inspection system according to the embodiment of the present invention compares each of six defect like object regions a, b, c, d, e and f in the picture at the instant t6, for example, with each of defect like regions in the five previous pictures at t1–t5 to calculate the distance and direction therebetween, and determines whether the distance and direction match the movement of the inspected surface 1. In the example shown in FIG. 7, the inspection system judges that the regions a and b are moving correctly, and hence they are actual defects. The regions c–f remaining stationary are regarded as noise. In the picture at t3, the region a disappears (or fails to be extracted), and therefore, the region a is not registered in the comparison of the picture at t6 with the picture at t3. However, in the comparison with the all the previous picture, the region a is registered four times, and the region b is registered three times. When M is set equal to 3, the inspection system finally judges each of the regions a and b to be a defect on the inspected surface.

In the example, defect-like object regions are extracted from a bright and dark striped picture. In this case, a region in a boundary between a bright zone and a dark zone might be extracted as a defect point, and misjudged as a defect if this extracted region happens to move with movement of the imaging area. To avoid such a false detection, the inspection system may be arranged to apply the defect extracting operation only to the bright zones, or the regions other than the boundaries. With the exclusion of the dark zones or of the boundaries, the inspection system can improve the accuracy of defect detection.

In the illustrated example, the relative movement between the inspected surface 1 and the imaging area A is a rectilinear movement along such a direction that a defect in an image moves in a direction perpendicular to the stripes of the striped pattern and parallel to the x axis, as shown in FIG. 2A. The stripes extends along the y axis.

According to one of various possible interpretations, the imaging step of the imaging producing step corresponds at least in part to the step S1 in FIG. 3 and the step S11 in FIG. 4, and the image processing step corresponds to the steps S2–S4 and S12–S26. The extracting step for image enhancement (or improvement) and extraction of a set of defect candidate regions may correspond to the step S2 and the step S12. The examining step may correspond to the step S3 and the steps S13–S24, and the deciding step may correspond to the step S25. The selecting step for selecting a subset of the set of the defect candidate regions may correspond to the steps S17 and S19, for example.

The image producing means corresponds to the CCD camera 2, the conveyor 8, and the illuminating or lighting arrangement 3, and the image processing means corresponds to the image processor 4 and the host computer 6 according to one of various possible interpretations.

The image processing means in the illustrated example of the present invention comprises an extracting means for image enhancement and extraction, an examining means connected with the extracting means to receive information from the extracting means, and a deciding means connected with the examining means to receive information from the examining means. The examining means may comprise a comparing means (S14, S16) for comparing candidate regions extracted from any two of the sequence of the pictures taken by the imaging means, a measuring means (S15) for determining a quantity of movement of the inspected surface 1 relative to the imaging area A, and a checking means (S17) for checking whether the separation between two candidate regions extracted from two of the pictures matches the quantity of movement of the inspected surface with a predetermined tolerance.

The comparing means is connected with the extracting means for receiving information on the extracted candidate regions, and the measuring means is connected with a distance signal producing means such as the pulse generator 7 for receiving the distance signal indicative of the distance traveled by the inspected surface relative to the imaging area of the imager. The imaging area is an area contained in the field of view of the CCD camera 2, for example. The checking means is connected with both the comparing means and the measuring means for receiving data from both means for check. The selecting means may be further comprised in the examining means and connected with the checking means. The deciding means is connected with the checking means through the selecting means or directly without the selecting means. The extracting means is further connected with the picture storage means for storing original and processed pictures. The examining means may further comprise a data storage means for storing data items about the extracted candidate regions for later use for comparison, checking and selection.

What is claimed is:

1. An inspection process for detecting a defect on an inspected surface of an object to be inspected, said inspection process comprising:

an image producing step of moving said inspected surface relative to an imaging area and forming a sequence of electronic pictures of the inspected surface within said imaging area; and an image processing step of extracting defect candidate regions from said pictures, of determining a spatial separation from a position of one candidate region extracted from a previous picture which is one of the pictures, to a position of another candidate region extracted from a subsequent picture which is one of the pictures formed after the previous picture in said image producing step, of determining whether said spatial separation is in agreement with a movement of said inspected surface relative to said imaging area, and of judging that there exists a defect in the inspected surface when said spatial separation is in agreement with said movement.

2. An inspection process as claimed in claim 1:

wherein said image producing step comprises;

a moving step of moving at least one of said object to be inspected, and an imaging means viewing said inspected surface in said imaging area; and an imaging step of forming said electronic pictures with said imaging means; and wherein said image processing step comprises;

an extracting step of extracting a set of the candidate regions from said sequence of the pictures;

an examining step of examining positions of the candidate regions extracted from at least two of the pictures, determining a quantity of a positional change from the position of one candidate region extracted from said previous picture, to the position of another candidate region extracted from said subsequent picture, and examining whether said quantity of the positional change is proportional to a quantity of movement of said inspected surface relative to said imaging area from a time of image formation of said previous picture to a time of image formation of said subsequent picture; and a deciding step of deciding that there exists a defect on the inspected surface and producing a defect detection signal when said quantity of the positional change is proportional to said quantity of the movement of said inspected surface.

3. An inspection process as claimed in claim 2 wherein said pictures are formed while a bright and dark pattern is projected in the imaging area on the inspected surface, so that each of said pictures is an image of the bright and dark pattern projected on the inspected surface.

4. An inspection process as claimed in claim 3 wherein each of said pictures formed by said imaging means comprises a bright zone and a dark zone; said extracting step is performed by extracting the candidate regions only from the bright zones of said pictures; and said examining step is performed by examining whether said quantity of the positional change between two of the candidate regions extracted from the bright zones is proportional to said quantity of the movement of said inspected surface.

5. An inspection process as claimed in claim 2 wherein said examining step comprises a selecting step of selecting a subset from said set of the candidate regions;

said subset comprises a plurality of said candidate regions;

each of the candidate regions of said subset is one candidate region extracted from a unique one of a subsequence of said sequence of the electronic pictures, so that the candidate regions of said subset are all different in time of image formation;

all the candidate regions of said subset are arranged in an order of time of image formation substantially in a straight line in an image plane of said imaging means;

each of the candidate regions of the subset is spaced from another of the candidate region of the subset at a distance which is substantially proportional to a distance traveled by said inspected surface from the time of image formation of each of the candidate regions of said subset to the time of image formation of another of the candidate regions of said subset; and said deciding step comprises an operation for allowing generation of said defect detection signal only when the number of the candidate regions of the subset selected in said selecting step is equal to or greater than a predetermined number.

6. An inspection process according to claim 1 wherein the image producing step comprises an operation for moving said inspected surface relative to said imaging area in a predetermined direction and an operation for forming the sequence of the electronic pictures of the inspected surface at different positions relative to the imaging area.

7. An inspection process according to claim 1 wherein the image producing step comprises a measuring operation for measuring a quantity of movement of said inspected surface relative to said imaging area, and the image processing step comprises a checking operation for comparing said spatial separation with the quantity of the movement to determine whether said spatial separation is in agreement with the movement of the said inspected surface.

8. An inspection system for detecting a defect in an inspected surface of an object to be inspected, said inspection system comprising:

an image producing means for moving said inspected surface relative to an imaging area and forming a sequence of electronic pictures of the inspected surface within said imaging area;

an image processing means for extracting defect candidate regions from said pictures, for determining a spatial separation from a position of one candidate region extracted from a previous picture which is one of the pictures, to a position of another candidate region extracted from a subsequent picture which is one of the pictures formed after the previous picture by said image producing means, for determining whether said spatial separation is in agreement with a movement of said inspected surface relative to said imaging area, and for judging that there exists a defect in the inspected surface when said spatial separation is in agreement with said movement.

9. An inspection system as claimed in claim 8:

wherein said image producing means comprises;

an imaging means for viewing said inspected surface in said imaging area, and forming said electronic pictures; and a moving means for moving at least one of said object to be inspected, and said imaging means; and wherein said image processing means comprises;

an extracting means for extracting a set of the candidate regions from the sequence of the pictures;

an examining means for examining positions of the candidate regions extracted from at least two of the pictures, for determining a quantity of a positional change from the position of one candidate region extracted from said previous picture, to the position of another candidate region extracted from said subsequent picture, and for examining whether said quantity of the positional change is proportional to a quantity of movement of said inspected surface relative to said imaging area from a time of image formation of said previous picture to a time of image formation of said subsequent picture; and a deciding means for producing a defect detection signal indicating that there exists a defect on the inspected surface when said positional change is proportional to the movement of said inspected surface.

10. An inspection system as claimed in claim 9 wherein said image producing means further comprises an illuminating means for projecting a bright and dark pattern on said inspected surface, so that each of the pictures produced by said imaging means is an image of the bright and dark pattern projected on the inspected surface and comprises a bright zone and a dark zone.

11. An inspection system as claimed in claim 10 wherein said image processing means further comprises a boundary recognizing means for recognizing a boundary between a bright zone and a dark zone in said pictures of the bright and dark pattern; and said extracting means includes a means for extracting said candidate regions in accordance with a change in luminance in a region other than said boundary.

12. An inspection system as claimed in claim 10 wherein said image processing means further comprises a picture storing means for storing said pictures sequentially produced by said imaging means, and said extracting means includes a means for extracting said candidate regions only from the bright zones of said pictures stored in said picture storing means.

13. An inspection system as claimed in claim 10 wherein said extracting means includes a means for extracting the candidate regions only from the bright zones of said pictures; and said examining means includes a means for examining only the positions of the candidate region extracted from the bright zones in the pictures.

14. An inspection system as claimed in claim 9 wherein said subsequent picture comprises one of the candidate regions and each of a plurality of said previous pictures comprises one of the candidate regions;

said examining means comprises;

a comparing means for comparing the candidate region extracted from said subsequent picture with the candidate regions extracted from each of the previous pictures formed sequentially before the subsequent image by said image producing means, to determine a quantity of displacement from the position of the candidate region extracted from each of the previous pictures to the position of the candidate region of said subsequent picture;

a measuring means for determining a quantity of movement of said inspected surface relative to said imaging area from an instant when each of said previous pictures is formed by said image producing means to an instant when said subsequent picture is formed by said image producing means; and a checking means for determining whether said quantity of displacement to the position of the candidate region extracted from the subsequent picture from the position of the candidate region extracted from each of the previous picture is proportional to said quantity of movement of said imaging area from the instant of formation of a corresponding one of the previous picture to the instant of formation of the subsequent picture, to determine whether each of the previous pictures is a conformable picture or not, said conformable picture being a picture comprising a conformable candidate region from which said quantity of displacement to the position of the candidate region in the subsequent picture is proportional to said quantity of movement of said inspected surface from the instant of image formation of the conformable picture to the instant of image formation of the subsequent picture; and said deciding means comprises a means for judging that the candidate region in the subsequent picture is a defect if the number of the conformable pictures is equal to or greater than a predetermined number.

15. An inspection system as claimed in claim 9 wherein said examining means comprises a selecting means for selecting a subset from said set of the candidate regions;

said subset comprises a plurality of said candidate regions;

each of the candidate regions of said subset is one candidate region extracted from a unique one of a subsequence of said sequence of the electronic pictures, so that the candidate regions of said subset are all different in time of image formation;

all the candidate regions of said subset are arranged in an order of the time of image formation substantially in a straight line in an image plane of said imaging means;

each of the candidate regions of the subset is spaced from another of the candidate region of the subset at a distance which is substantially proportional to a distance traveled by said inspected surface from the time of image formation of each of the candidate regions of said subset to the time of image formation of another of the candidate regions of said subset; and said deciding means comprises a means for allowing generation of said defect detection signal only when the number of the candidate regions of the subset selected in said selecting step is equal to or greater than a predetermined number.

16. An inspection system as claimed in claim 15 wherein said predetermined number is equal to or greater than three, said subsequence comprises a first selected picture which is one of said pictures of said sequence and a last selected picture which is one of said pictures of said sequence and which follows after said first selected picture in said sequence, and an intermediate picture which is intermediate between said first and last selected pictures in said sequence is excluded from said subsequence.

17. An inspection system according to claim 8 wherein the image producing means comprises a machine for moving said inspected surface relative to said imaging area in a predetermined direction along a straight line and a device for measuring the movement of the inspected surface relative to the imaging area.

18. An inspection system for detecting a defect on an inspected surface of an object to be inspected, said inspection system comprising:

an image producing subsystem for moving the inspected surface relative to an imaging area along a predetermined direction from a previous position to a subsequent position and forming a previous picture of the inspected surface within said imaging area at a previous time instant when the inspected surface is located at the previous position, and a subsequent picture of the inspected surface within the imaging area at a subsequent time instant when the inspected surface is located at said subsequent position; and an image processing subsystem for extracting defect candidate regions as a candidate for a defect from said previous and subsequent pictures, for determining an image movement from an image location of the candidate region in said previous picture to an image location of the candidate region in said subsequent picture, for comparing said image movement with a movement of the inspected surface from said previous position to said subsequent position, and for producing a defect detection signal representing presence of a defect when said image movement is substantially in proportion to the movement of the inspected surface from the previous position to the subsequent position.

19. An inspection system as claimed in claim 18:

wherein said image producing means comprises:

an imager for producing a time series of pictures of said inspected surface within said imaging area, said previous and subsequent pictures being two of the pictures in said time series;

an illuminating means for illuminating said inspection surface in said image area; and a moving means for producing relative motion between said inspected surface and said imager so that said inspected surface moves along a predetermined rectilinear direction in said imaging area, and producing a distance signal representing a distance traveled by said inspected surface in said imaging area; and wherein said image processing means comprises:

a picture storage means for storing image data representing said time series of the picture;

an extracting means for extracting candidate regions from said time series of the pictures stored in said storage means;

an examining means for arranging said candidate regions extracted from said time series of the pictures in pairs each of which consisting of a first mate which is one candidate region extracted from said previous picture and a second mate which is one object region extracted from said subsequent picture, for determining the image movement between said first and second mates of each pair, for determining whether each pair is a matched pair or not by determining whether the image movement of each pair is substantially proportional to the movement of the inspected surface from the previous position to the subsequent position, and for grouping said matched pairs into a group of the matched pairs each of which comprises a single common one of the candidate regions; and a deciding means for producing the defect detection signal when a number of the matched pairs in the group is equal to or greater than a predetermined number.

20. An inspection system as claimed in claim 18 wherein said illuminating means includes a means for projecting a bright and dark pattern on the inspected surface, said imaging area determined by said imager and said bright and dark pattern are held stationary, and said moving means comprises a conveyor for moving said object having said inspected surface so that an image point of a scene point fixed on the inspected surface moves along one of horizontal and vertical directions in an image plane of the imager.

21. An inspection system according to claim 18 wherein the image producing subsystem comprises a conveyor for moving the inspected surface relative to the imaging area, a detecting device for detecting the movement of the inspected surface relative to the imaging area and generating a distance signal representing a quantity of the movement, and a camera for forming pictures of the inspected surface within the imaging area and producing a video signal, and wherein the image processing subsystem is connected with the detecting device and the camera, and receives the distance signal and the video signal.

* * * * *